US 11,504,138 B2

(12) United States Patent
Cameron, Jr. et al.

(10) Patent No.: US 11,504,138 B2
(45) Date of Patent: Nov. 22, 2022

(54) ROTARY SURGICAL INSTRUMENT ASSEMBLY

(71) Applicant: DEPUY IRELAND UNLIMITED COMPANY, County Cork (IE)

(72) Inventors: Rod G. Cameron, Jr., Raynham, MA (US); John Cuneo, Raynham, MA (US); Chad McAlexander, Warsaw, IN (US); Prasenjit Saha, Warsaw, IN (US)

(73) Assignee: DEPUY IRELAND UNLIMITED COMPANY

( * ) Notice: Subject to any disclaimer, the term of this patent is extended or adjusted under 35 U.S.C. 154(b) by 115 days.

(21) Appl. No.: 16/652,207

(22) PCT Filed: Oct. 1, 2018

(86) PCT No.: PCT/US2018/053754
§ 371 (c)(1),
(2) Date: Mar. 30, 2020

(87) PCT Pub. No.: WO2019/070580
PCT Pub. Date: Apr. 11, 2019

(65) Prior Publication Data
US 2020/0246024 A1    Aug. 6, 2020

Related U.S. Application Data

(60) Provisional application No. 62/567,806, filed on Oct. 4, 2017.

(51) Int. Cl.
*A61B 17/16* (2006.01)
*A61B 17/00* (2006.01)

(52) U.S. Cl.
CPC ...... *A61B 17/1666* (2013.01); *A61B 17/1615* (2013.01); *A61B 2017/00526* (2013.01)

(58) Field of Classification Search
CPC ............ A61B 17/1666; A61B 17/1684; A61B 17/1664
See application file for complete search history.

(56) References Cited

U.S. PATENT DOCUMENTS 7,632,276 B2    12/2009  Fishbein
2011/0202060 A1*  8/2011  White ................ A61B 17/1666
606/80

(Continued)

FOREIGN PATENT DOCUMENTS

EP    3178417 A1    6/2017
WO    90/07908 A1    7/1990

OTHER PUBLICATIONS

PCT/US2018/053754—International Search Report dated Mar. 6, 2019.

*Primary Examiner* — Samuel S Hanna

(57) ABSTRACT

A rotary surgical assembly is disclosed. The assembly has a plurality of cutting teeth (216), a hollow dome (200) and a spindle (10). The hollow dome has a pole having a pole axis X, and a cutting surface featuring some of the cutting teeth. The cutting surface includes a curved part (214) and a substantially flat part (212) proximal the pole with an aperture (210) extending therethrough. The spindle has a proximal end (12) and a distal end (14) including a spindle mounting element (16). The spindle mounting element is secured to the dome beneath the substantially flat part of the cutting surface. The spindle mounting element has a cutting tooth (22) that extends distally through the cutting surface's aperture to form one of the said plurality of cutting teeth. A kit, and methods of manufacturing the rotary surgical assembly are described also.

12 Claims, 8 Drawing Sheets

(56) References Cited

U.S. PATENT DOCUMENTS

2014/0271005 A1    9/2014   Xie et al.
2016/0278792 A1    9/2016   Victor
2017/0164955 A1    6/2017   Victor \* cited by examiner

ROTARY SURGICAL INSTRUMENT ASSEMBLY

This application is a National Stage Application filed Under 35 U.S.C. § 371 of International Application No. PCT/US2018/053754 filed Oct. 1, 2018, which claims priority to U.S. 62/567,806 filed Oct. 4, 2017, which are both hereby incorporated by reference in their entireties.

TECHNICAL FIELD

The present disclosure relates generally to orthopaedic surgical instruments and more particularly to rotary orthopaedic instruments, such as an acetabular grater, used for joint arthroplasty.

BACKGROUND

Joint arthroplasty is a well-known surgical procedure by which a diseased and/or damaged natural joint is replaced by a prosthetic joint. For example, in a hip arthroplasty surgical procedure, a prosthetic hip replaces a patient's natural hip. A typical prosthetic hip includes an acetabular orthopaedic prosthesis and/or femoral head orthopaedic prosthesis. A typical acetabular orthopaedic prosthesis includes an acetabular cup, which is secured to the patient's natural acetabulum, and an associated polymer bearing or ring.

To facilitate the replacement of the natural joint with an acetabular orthopaedic prosthesis, orthopaedic surgeons use a variety of orthopaedic surgical instruments such as, reamers, drill guides, drills, and/or other surgical instruments.

Acetabular graters are used to prepare the acetabulum for receipt of an acetabular cup. Conventionally, the connection interface between the grater and a removable driver is provided by a cross-back or bow-tie design.

There is a need for a connection interface that has a reduced cost of manufacture associated with it, and which provides an improved cutting efficiency and durability across all of the size ranges.

SUMMARY OF THE INVENTION

According to an aspect of the invention, there is a rotary surgical assembly attachable to a driver, the assembly comprising:
  a plurality of cutting teeth;
  a hollow dome comprising
    a pole having a pole axis, and
    a cutting surface on which is provided at least some of said plurality of cutting teeth, said cutting surface including a curved part and a substantially flat part proximal the pole, the substantially flat part having an aperture extending therethrough; and
  a spindle having a proximal end for connection to the driver and a distal end including a spindle mounting element, in which a part of the spindle mounting element is secured to an internal surface of the dome beneath the substantially flat part of the cutting surface, and in which said spindle mounting element comprises a cutting tooth which extends distally through the aperture extending through the substantially flat part of the cutting surface to form one of the said plurality of cutting teeth.

In some constructions of the assembly, the spindle is monolithic. This may be achieved, for instance by manufacturing the spindle using metal injection moulding or three-dimensional printing. In some constructions, the cutting tooth may be mountable on the spindle mounting element.

In some constructions, the surface normal of the substantially flat part of the cutting surface is substantially parallel to the pole axis. The substantially flat surface of the cutting surface may be substantially circular and centred on the pole axis.

In some constructions, the spindle mounting element is secured to the internal surface of the dome by a brazed, soldered or welded joint. The spindle mounting element may comprise a distally located platform having a substantially flat distally facing surface on which the cutting tooth is provided. The platform provides an enlarged surface area for the formation of the brazed, soldered or welded joint. This ensures that the spindle is securely connected to the dome. The substantially flat distal surface of the platform of the spindle mounting element may be secured to the substantially flat surface of the cutting surface by means of a brazed, soldered or welded joint.

The aperture that extends through the substantially flat part of the cutting surface of the dome, in some constructions, takes the form of an elongate slot. The cutting tooth may be provided on a pedestal that extends distally from the substantially flat, distally facing surface of the platform. The pedestal may be shaped to form a snug fit within the elongate slot. A brazed, soldered or welded joint may be formed between the outer surface of the pedestal and the inner surface of the aperture. This further increases the strength of the connection between the spindle and the dome.

The pedestal may include a lip having an inner surface which abuts an outer edge of the platform. The lip has a radius of curvature that follows the curvature of the border of the circular, substantially flat surface, which may be between about 6 mm and about 9 mm, and more preferably about 7.5 mm.

The cutting tooth on the spindle forms a polar cutting tooth. The tooth has a cutting edge that causes cutting of the acetabulum about the pole when the dome of the acetabular grater is rotated about the polar axis. In some constructions, the polar cutting tooth extends outwardly from a position at or near the pole axis towards a border of the substantially circular and substantially flat part of the cutting surface. The cutting tooth is designed such that when the spindle is secured to any diameter of grater, the polar cutting tooth (in combination with the other cutting teeth) forms an optimal cutting surface across the entire range of grater sizes with minimal deviation (i.e., over reaming or under reaming) in the cutting profile.

In order to reduce the likelihood of deviation in the cutting profile still further, it is envisaged that in some constructions, a first spindle having a design of polar cutting tooth with a first cutting edge geometry is attached to a first subset of domes and a second spindle having a design of polar cutting tooth with a second cutting edge geometry is attached to a second subset of domes.

In some constructions, the cutting edge of the polar tooth on the first spindle may comprise a radius of curvature that is different from the radius of curvature of the cutting edge of the polar tooth on the second spindle.

For example, the first subset of domes may include a plurality of domes each having a diameter in the range of between "a" and "b", and the second subset of domes may include domes each having a diameter in the range of between "c" and "d", in which the diameter of domes in the range "a-b" is less than the diameter of domes in the range "c-d".

In some constructions, a first spindle having a design of polar cutting tooth with a first cutting edge geometry is attached to a first subset of domes, a second spindle having a design of polar cutting tooth with a second cutting edge geometry is attached to a second subset of domes and at least a further spindle having a design of polar cutting tooth with a cutting edge geometry that is different to the cutting edge geometry of the first spindle and the second spindle is attached to at least one further subset of domes, the at least one further subset of domes includes domes having a diameter that is greater than or less than the range a-b and c-d.

It is envisaged, for example, that a first subset includes domes that each have a dome diameter in the range of 36 mm to 43 mm; a second subset includes domes that each have a dome diameter in the range of 44 mm to 55 mm and a third subset includes domes that each have a dome diameter in the range of 56 mm to 66 mm.

In some constructions, the cutting tooth on the spindle mounting element has a curved cutting edge which follows at least part of the curvature of the curved surface of the dome. The curved cutting edge may have a radius of curvature between about 21 mm and about 25 mm, preferably of about 23 mm.

The inventors have recognised that a cutting tooth having a dual-radius of curvature along the cutting edge reduces the deviation in the cut profile when the spindle is mounted to different sizes of acetabular grater. Therefore, in some constructions, the curved cutting edge comprises a first cutting area having a first radius of curvature and a second cutting area having a second radius of curvature. The first radius of curvature may be less than the second radius of curvature. The second cutting area may extend outwardly from a position at, or near the pole axis towards the border of the substantially circular and substantially flat part of the cutting surface, and the first cutting area extends outwardly from the second cutting area towards the border of the substantially circular and substantially flat part of the cutting surface. The first cutting area may have a radius of curvature between about 18 mm and about 22 mm and the second cutting area may have a radius of curvature between about 24 mm and about 28 mm. In some preferred constructions, the first cutting area has a radius of curvature between about 19 mm and about 21 mm and the second cutting area has a radius of curvature between about 25 mm and about 27 mm. In some even more preferred constructions, the first cutting area has a radius of curvature of about 20 mm and the second cutting area has a radius of curvature of about 26.5 mm.

According to second aspect of the invention, the rotary surgical assembly as described herein is a grater, such as an acetabular grater.

According to a third aspect of the invention, there is provided a kit comprising the rotary surgical assembly as described herein and a driver.

According to a fourth aspect of the invention, there is provided a kit comprising:
 a first rotary surgical assembly comprising
  a plurality of cutting teeth;
  a hollow dome having a first diameter and comprising
   a pole having a pole axis, and
   a cutting surface on which is provided at least some of said plurality of cutting teeth, said cutting surface including a curved part and a substantially flat part proximal the pole, the substantially flat part having an aperture extending therethrough; and
  a spindle having a proximal end for connection to the driver and a distal end including a spindle mounting element, in which a part of the spindle mounting element is secured to an internal surface of the dome beneath the substantially flat part of the cutting surface, and in which said spindle mounting element comprises a cutting tooth which extends distally through the aperture in the substantially flat part of the cutting surface to form one of the said plurality of cutting teeth; and
 a second rotary surgical assembly comprising:
  a plurality of cutting teeth;
  a hollow dome having a second diameter which is greater or less than the first diameter, said dome comprising
   a pole having a pole axis, and
   a cutting surface on which are provided at least some of said plurality of cutting teeth, said cutting surface including a curved part and a substantially flat part proximal the pole, the substantially flat part having an aperture extending therethrough, and
   a spindle having a proximal end for connection to the driver and a distal end including a spindle mounting element, in which a part of the spindle mounting element is secured to an internal surface of the dome beneath the substantially flat part of the cutting surface, and in which said spindle mounting element comprises a cutting tooth which extends distally through the aperture in the substantially flat part of the cutting surface to form one of the said plurality of cutting teeth,
in which the spindle connected to the dome in the first rotary surgical assembly is the same size and shape as the spindle connected to the dome in the second rotary surgical assembly.

Each of the first and second rotary surgical assemblies may be a grater, for example, an acetabular grater.

According to a still further aspect of the invention, there is provided a method of manufacturing a rotary surgical assembly as herein described, which comprises the steps of:

(i) forming a hollow dome comprising a pole having a pole axis, and a cutting surface on which are provided a plurality of cutting teeth, said cutting surface including a curved surface and a substantially flat part proximal the pole, the substantially flat part having an aperture extending therethrough;

(ii) forming a spindle having a proximal end for connection to the driver and a distal end including a spindle mounting element, in which a part of the spindle mounting element is securable to an internal surface of the dome beneath the substantially flat part of the cutting surface, and in which said spindle mounting element comprises a cutting tooth;

(iii) connecting the spindle to the hollow dome, such that the cutting tooth on the spindle mounting element extends through the aperture in the substantially flat part of the cutting surface of the dome.

Optionally, the step of connecting the spindle to the hollow dome comprises the step of brazing, welding or soldering a surface of the spindle mounting element to the internal surface of the dome.

Optionally, the step of forming the hollow dome with cutting teeth comprises applying a chemical etch to a blank to form the plurality of cutting teeth. This step may also comprise forming a slot beneath the curved cutting edge of each of the plurality of cutting teeth. This slot facilitates the removal of bone fragments/chips from the cutting surface for collection within the hollow inner surface of the dome.

The step of forming the hollow dome may comprise hydroforming the dome from a blank.

The step of forming the hollow dome may also comprise the step of applying a chemical etch to the hydroformed dome. This step sharpens the cutting edge of each cutting tooth.

The step of forming the spindle may comprise;
   using a mixture comprising a powder of at least one metal or metal alloy;
   forming the spindle from the mixture using a metal-injection-molding process.

The step of forming the spindle may comprise the method of three-dimensional printing.

The step of forming the spindle may comprise the method of machining from a stock.

According to a still further aspect of the invention, there is provided a method of use of the rotary surgical assembly as herein described, which includes;
   coupling the proximal end of the spindle of the rotary surgical assembly to a driver;
   placing the rotary surgical assembly into a surgical site of a patient;
   using the rotary surgical assembly to remove tissue from the surgical site.

According to yet a still further aspect of the invention, there is provided a method of preparing a joint of a patient for a joint replacement comprising:
   coupling the proximal end of the spindle of the rotary surgical assembly of as herein described to a driver;
   using the rotary surgical assembly to remove tissue from the joint.

The rotary surgical assembly may be an acetabular grater, which removes tissue from the acetabulum.

BRIEF DESCRIPTION OF THE INVENTION

Constructions of a rotary surgical assembly embodied as an acetabular grater, will be described hereinafter, by way of example only, with reference to the accompanying drawings in which like reference signs relate to like elements and in which:

FIG. 1 shows a side view of a first construction of a spindle 10 for connection to a dome 200 of an acetabular grater.

Figure 1:
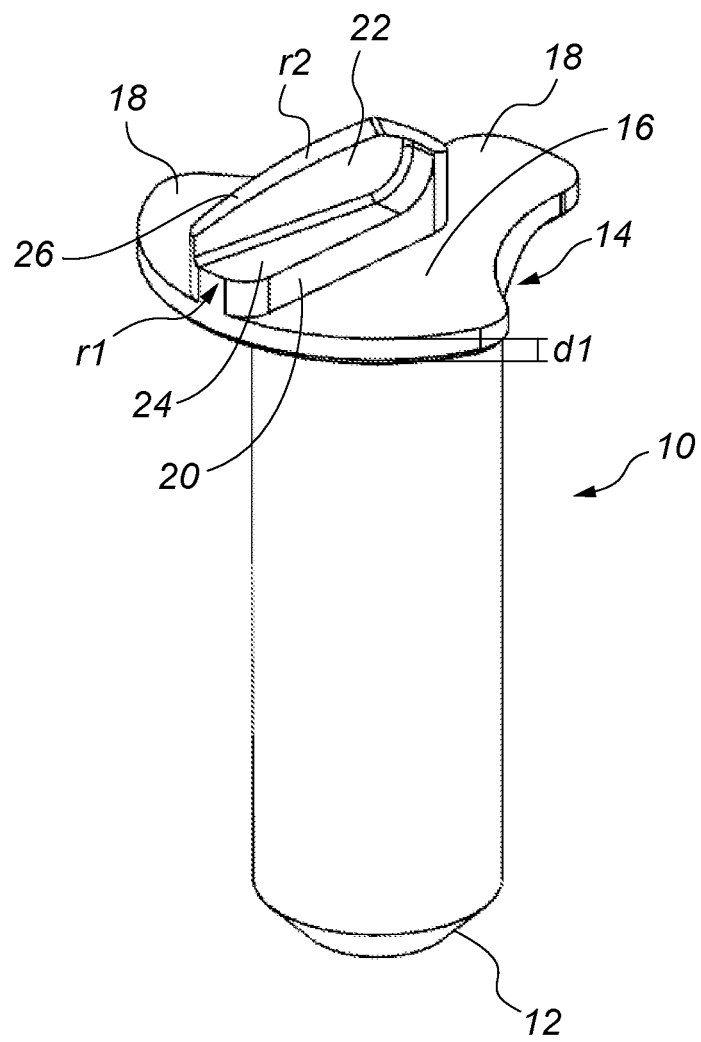
FIG. 1 shows a side view of a first construction of a spindle for connection to a dome of an acetabular grater.

The spindle 10 has a proximal end 12 and a distal end 14. The proximal end 12 is configured for connection to a driver. The distal end 14 of the spindle includes a spindle mounting element in the form of a platform 16. At least a part of the distal surface 18 of the platform 16 is substantially flat. This surface is secured to the internal surface of the dome of the acetabular grater (not shown) by a brazed joint.

Figure 4:
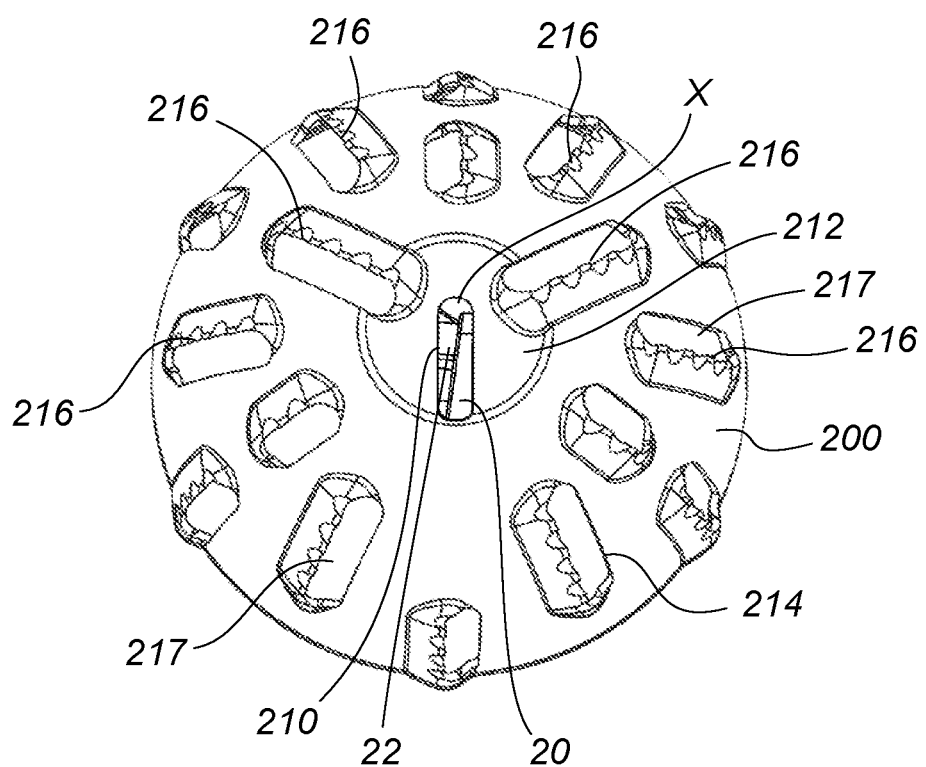
FIG. 4 shows a side view of the acetabular grater of FIG. 3.

A pedestal 20 is integrally formed on, or mounted onto the distal surface 18 of the platform 16. As shown in FIG. 4, the pedestal is configured to be received in a snug fit relationship within an elongated slot 210 within a substantially circular, substantially flat surface 212 of a cutting surface of a dome of the acetabular grater 200. The pedestal has a radius ($r_1$) of between about 6 mm and 9 mm, more preferably about 7.5 mm.

A cutting tooth 22 is integrally formed on, or mounted onto the distal surface 24 of the pedestal. The cutting tooth has a curved cutting edge 26 with a single radius ($r_2$) of curvature of between about 21 mm and about 25 mm, more preferably of about 23 mm.

Figure 2:
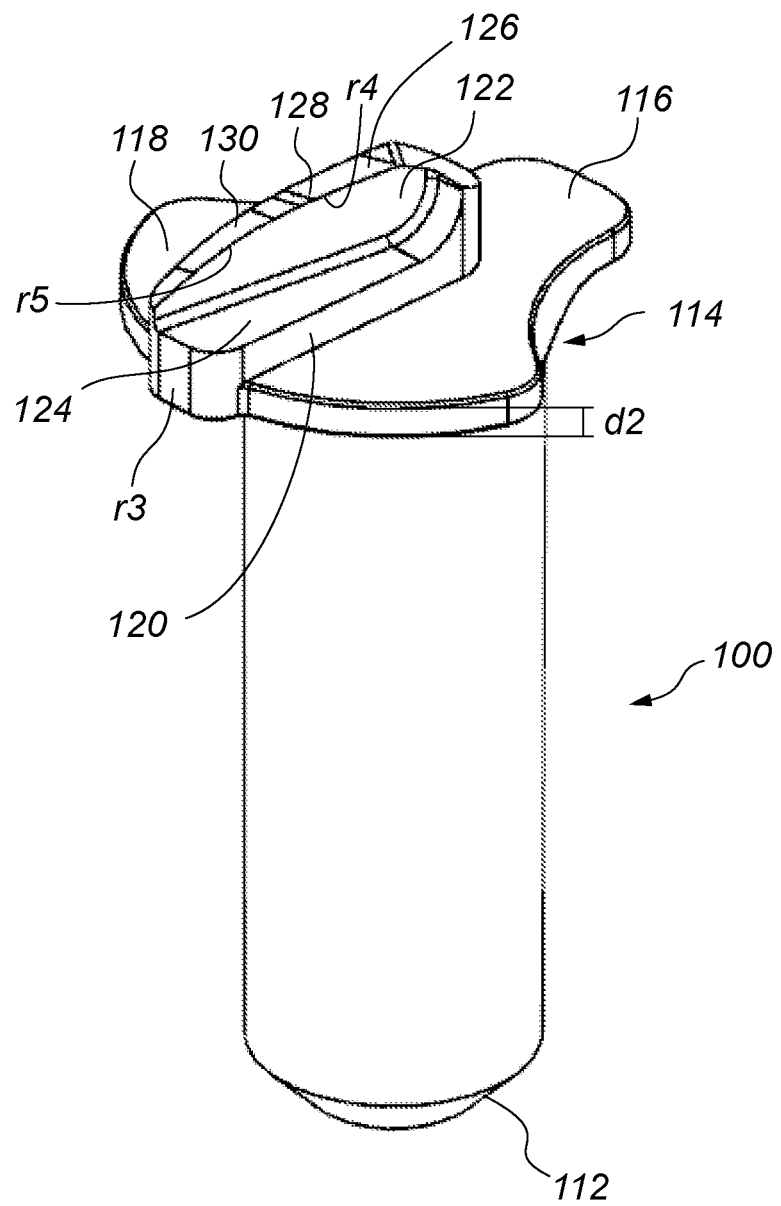
FIG. 2 shows a side view of a second construction of a spindle for connection to a dome of an acetabular grater.

FIG. 2 shows a side view of a second construction of a spindle 100 for connection to a dome 200 of an acetabular grater.

The spindle 100 has a proximal end 112 and a distal end 114. The proximal end 112 is configured for connection to a driver. The distal end 114 of the spindle includes a spindle mounting element in the form of a platform 116. At least a part of the distal, substantially flat surface 118 of the platform 116 is secured to the internal surface of the dome of the acetabular grater (not shown) by a brazed joint.

A pedestal 120 is integrally formed on, or mounted onto the distal surface 118 of the platform 16. As shown in FIG. 4, the pedestal is configured to be received in a snug fit relationship within an elongated slot 210 within a circular, substantially flat surface 212 of a cutting surface of a dome of the acetabular grater 200. The pedestal has a radius ($r_3$) of between about 6 mm and 9 mm, more preferably about 7.5 mm.

A polar cutting tooth 122 is integrally formed on, or mounted onto the distal surface 124 of the pedestal. The cutting tooth has a curved cutting edge 126 with a dual radius of curvature. A first cutting area 128 has a first radius of curvature and a second cutting area 130 has a second radius of curvature. The first radius of curvature ($r_4$) is less than the second radius of curvature ($r_5$). When the spindle is mounted to the dome of the acetabular grater, the first cutting area 128 extends outwardly from a position at, or near the pole axis (X) towards the border of the circular, substantially flat surface 212, and the second cutting area extends outwardly from the first cutting area towards the border of the substantially circular, substantially flat surface. The first cutting area 128 has a radius of curvature ($r_4$) from between about 18 mm and about 22 mm, more preferably about 20 mm. The second cutting area 130 has a radius of curvature ($r_5$) from between about 24 mm and about 28 mm, more preferably about 26.5 mm.

Figure 3:
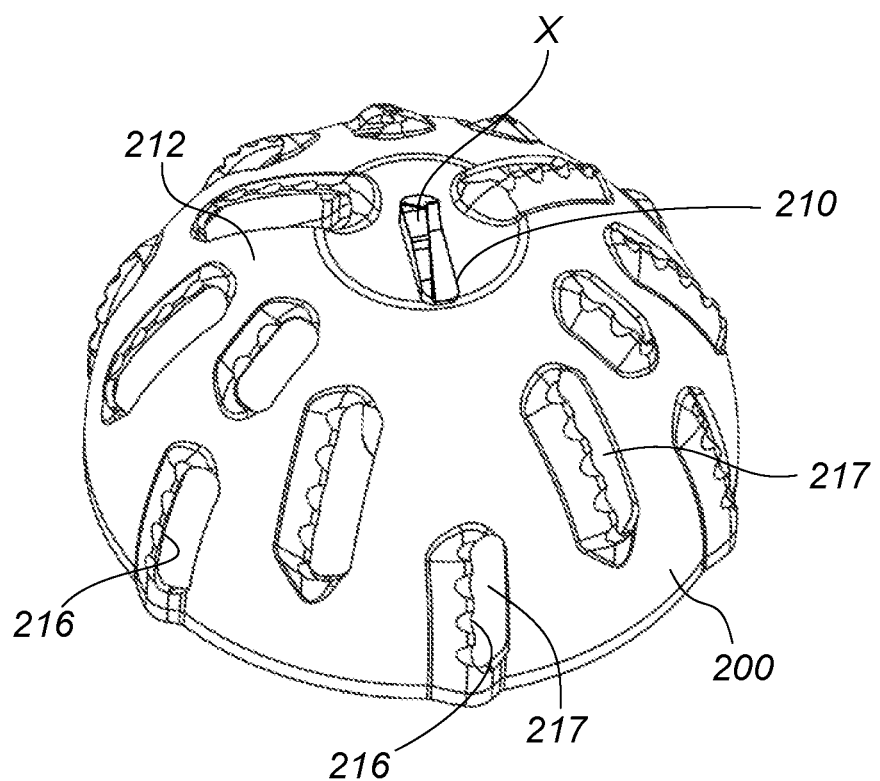
FIG. 3 shows a bottom view of an acetabular grater of the invention with the first construction of the spindle secured to the dome.
Figure 5:
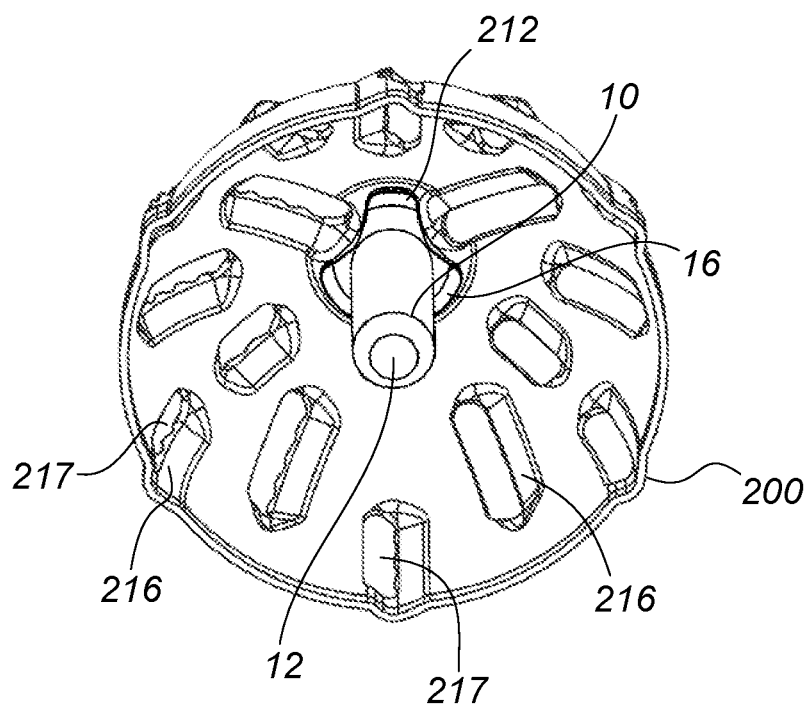
FIG. 5 shows a top view of the acetabular grater of FIG. 4.

FIGS. 3 to 5 show side, top and bottom views, respectively, of the first construction of the spindle 10 connected to the hollow dome 200 of an acetabular grater. The assembly formed by the connection of the second construction of the spindle 110 to the hollow dome of the acetabular grater is similar to the assembly shown here.

The dome 200 includes a cutting surface which includes a curved surface 214 and a substantially circular and substantially flat part of the cutting surface 212. This substantially circular and substantially flat surface is centred about a pole axis (X). The elongated slot 210 is provided within this surface. The surfaces 212 and 214 are provided with a plurality of cutting teeth 216. Adjacent to each cutting tooth 216 is a slot 217 which enabled bone chips and debris to be transferred away from the cutting surface and collect within the hollow dome.

Conventional acetabular graters have a ring geometry or include a cross bar to increase the stiffness of the device.

With the removal of these features within the rotary surgical device described herein, it is envisaged that alternative strengthening features are incorporated into the dome in order to compensate for the reduction in mechanical strength and thus the increased likelihood of deformation. These strengthening features can take the form of, for example, an increased thickness in the material in at least part of the dome or an additional portion of material provided about the perimeter of the rim of the dome.

When the spindle 10 is secured to the internal surface of the substantially circular, substantially flat surface 212 of the dome 200, the pedestal 20 of the spindle mounting element is in a snug-fit relationship with the elongated slot 210. A brazed joint may be formed between the pedestal 20 and the elongated slot 210. As shown in FIG. 4, the cutting tooth 22 extends through the elongated slot to form a polar tooth 22.

Figure 6:
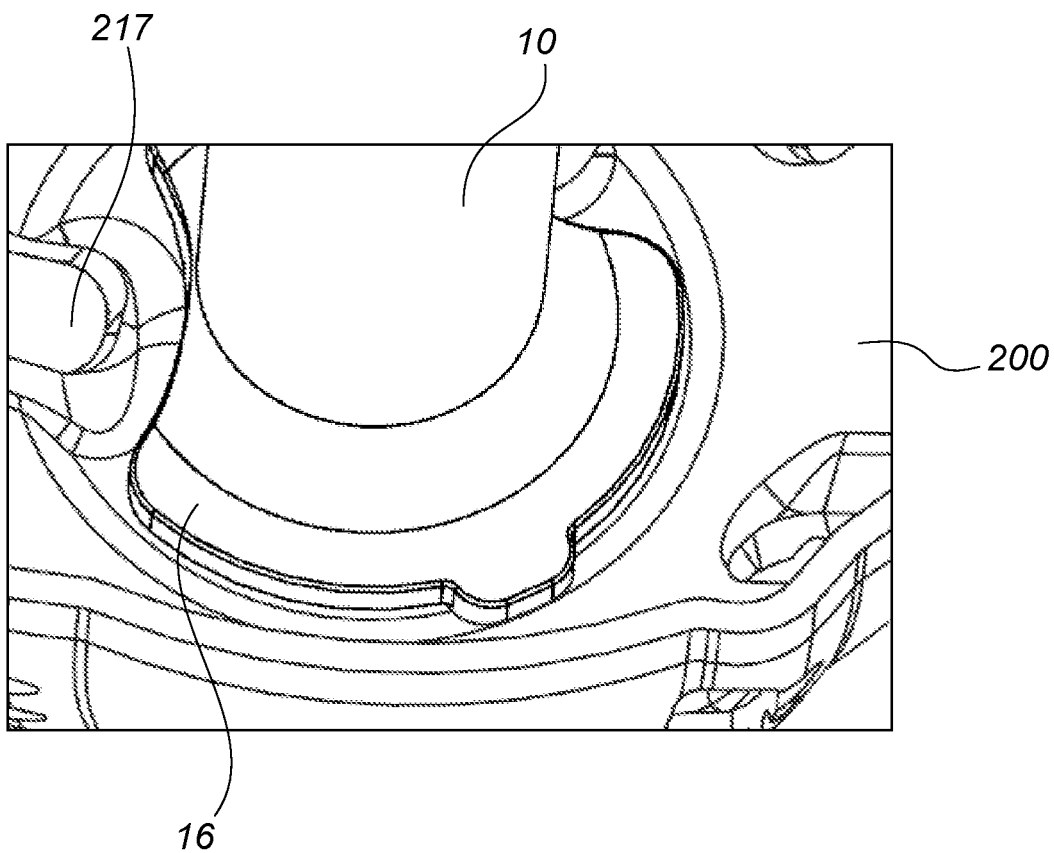
FIG. 6 shows a bottom view of an acetabular grater of the invention with the second construction of the spindle secured to the dome.

As shown in FIGS. 5 and 6, the platform 16 of the spindle 10 is designed such that when the spindle is connected to the dome 200 of the acetabular grater, the platform of the spindle mounting element does not obstruct the slot 217 associated with each cutting tooth 216.

Optimally, the design of the polar cutting tooth is such that the same design can be used across all available diameters of dome.

It was found that when a single design of polar cutting tooth 22 with a cutting edge having a single radius of curvature and having been optimized for use with a size 46 grater was used across the entire size range (sizes 36 to 66), it was found that a deviation in the cut profile was created between the cutting edges of the cutting teeth 216 and the cutting edge of the polar cutting tooth 22.

The deviation was measured relative to the cut profile (the assumed true ream profile) created by the cutting teeth 216.

The deviation was measured at two locations: (a) at a first end of the polar cutting tooth adjacent to the pole of the dome and (b) at the opposing second end of the cutting edge of the polar cutting tooth. It was assumed that the deviation caused at any intermediate location will be within this boundary. The deviation was measured in millimetres (mm).

Figure 7A:
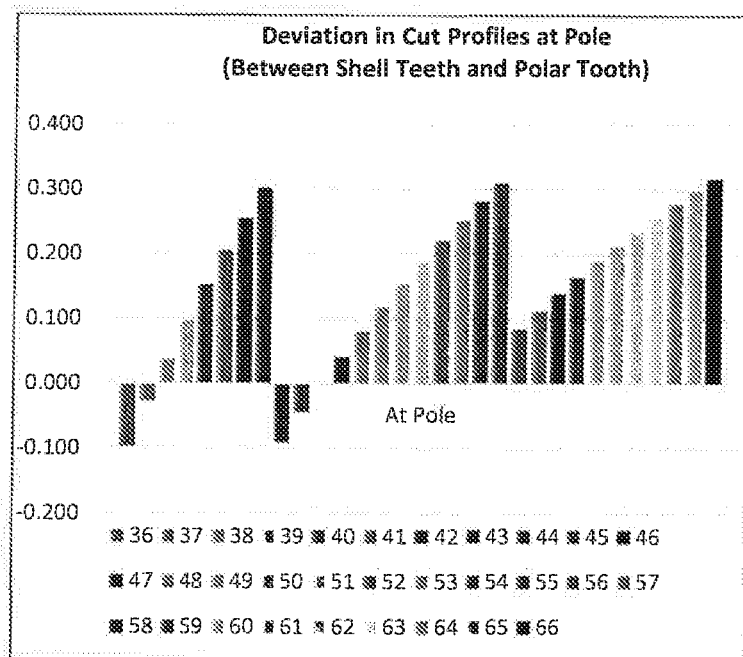
FIG. 7 shows the deviation in the cut profile achieved with a single radius cutting edge at (a) the pole and (b) the edge.
Figure 7B:
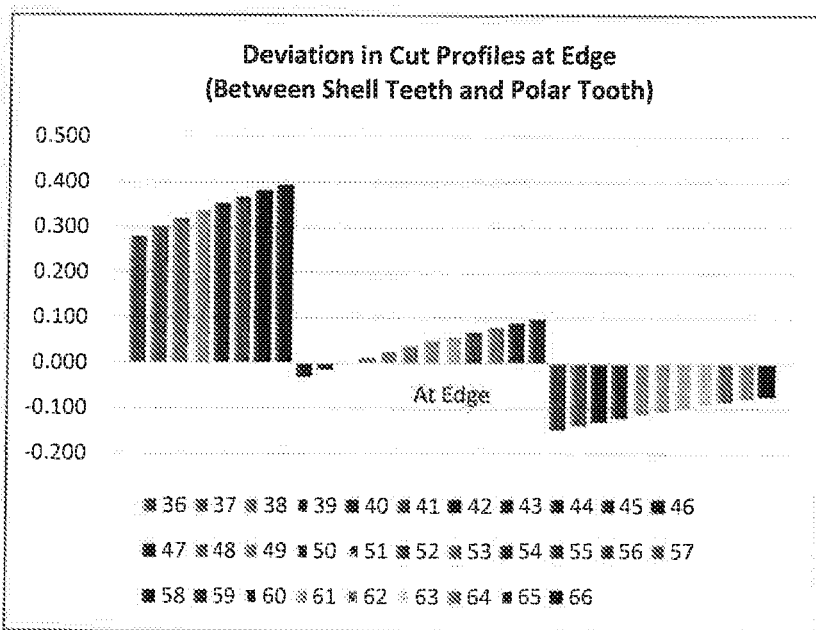

FIG. 7 shows the deviation in the cut profile from the assumed true ream profile achieved with a single radius cutting edge at (a) the pole and (b) the opposing radial end of the cutting edge.

As illustrated, the deviation in the cut profile ranged from +0.3 mm to −0.15 mm. A positive (+ve) value is representative of over reaming. A negative value (−ye) is representative of an undercut at the pole.

Figure 8A:
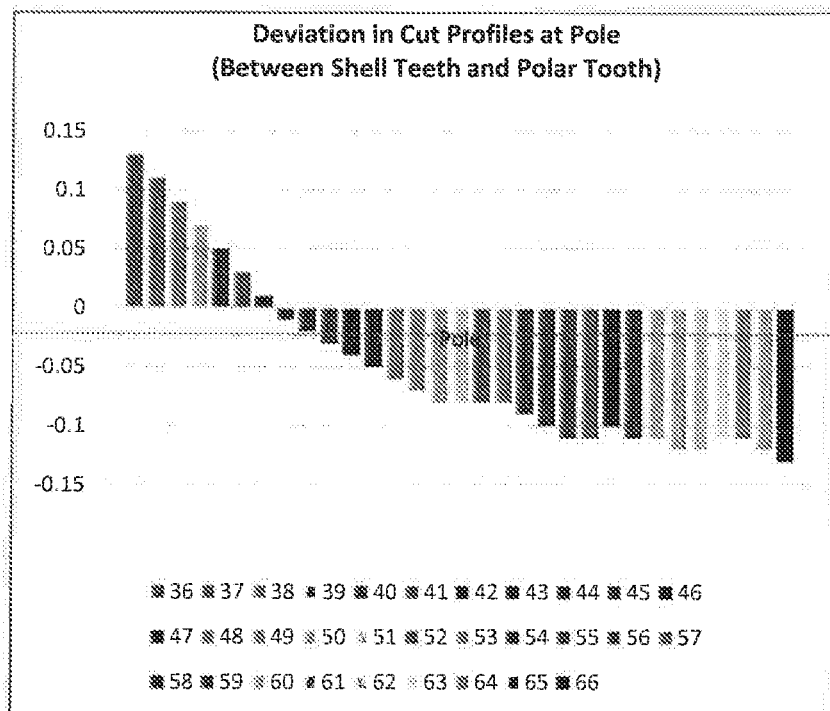
FIG. 8 shows the deviation in the cut profile achieved with a dual radius cutting edge at (a) the pole and (b) the edge.
Figure 8B:
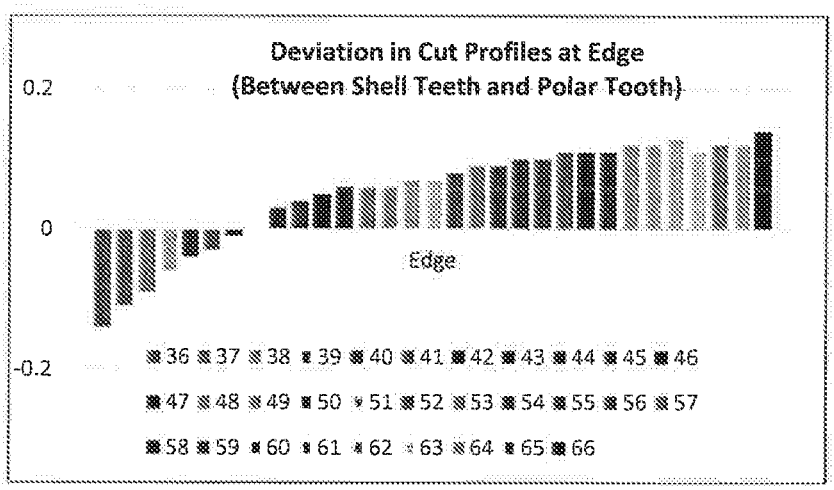

The deviation in the cut profile from the assumed true ream profile was observed to reduce when the cutting edge of the polar cutting tooth 22 has a dual radius of curvature. As illustrated in FIGS. 8a and 8b, the deviation ranged from +0.14 mm to −0.12 mm.

Although particular constructions of the invention have been described, it will be appreciated that many modifications/additions and/or substitutions may be made within the scope of the claimed invention.

The invention claimed is:

1. A rotary surgical assembly attachable to a driver, the assembly comprising:
    a plurality of cutting teeth;
    a hollow dome comprising
        a pole having a pole axis, and
        an external cutting surface on which is provided at least some of said plurality of cutting teeth, said cutting surface including a curved part and a substantially flat part proximal the pole, the substantially flat part having an elongated aperture extending therethrough; and
    a spindle having a proximal end for connection to the driver and a distal end including a spindle mounting element, the spindle mounting element comprises a platform having a planar distally facing surface, and a planar proximally facing surface opposite the planar distally facing surface, and the spindle comprises a spindle shaft extending proximally from the planar bottom surface to the proximal end, and a pedestal having a cutting tooth extending distally from the planar top surface, in which a part of the spindle mounting element is secured to an internal surface of the dome beneath the substantially flat part of the cutting surface, and in which said cutting tooth extends distally through the elongated aperture in the substantially flat part of the cutting surface to form one of said plurality of cutting teeth and the planar top surface of the mounting element abuts the internal surface of the hollow dome beneath the substantially flat part of the external cutting surface and the pedestal is received in a snug fit relationship within the elongated aperture to rotationally secure the spindle to the hollow dome, wherein the spindle is of a monolithic construction.

2. The rotary surgical assembly of claim 1, in which the substantially flat part of the cutting surface is substantially circular and is centered on the pole axis.

3. The rotary surgical assembly of claim 2, in which the cutting tooth on the spindle mounting element extends outwardly from a position at or near the pole axis towards a border of the substantially circular, substantially flat part of the cutting surface.

4. The rotary surgical assembly of claim 3, in which the cutting tooth has a curved cutting edge which follows at least part of a curvature of the curved surface of the dome.

5. The rotary surgical assembly of claim 4, in which the curved cutting edge comprises a first cutting area having a first radius of curvature and a second cutting area having a second radius of curvature.

6. The rotary surgical assembly of claim 5, in which the first radius titre is smaller than the second radius of curvature.

7. The rotary surgical assembly of claim 5, in which the econ ting area extends outwardly from a position at, or near the pole axis towards the border of the substantially circular, substantially flat part of the cutting surface, and the first cutting area extends outwardly from the second cutting area towards the border of the substantially circular, substantially flat part of the cutting surface.

8. The rotary surgical assembly of claim 5, in which the first cutting area has a radius of curvature between about 18 mm and about 22 mm and the second cutting area has a radius of curvature between about 24 mm and about 28 mm.

9. The rotary surgical assembly of claim 1, in which the pedestal includes an edge of a distal surface which abuts an outer edge of the platform.

10. The rotary surgical assembly of claim 9, in which the edge of the distal surface has a radius of curvature that follows a curvature of a border of the substantially flat part of the cutting surface.

11. The rotary surgical assembly of claim 10, in which the radius of curvature of the edge of the distal surface is between about 6 mm and about 9 mm.

12. The rotary surgical assembly of claim 1, in which the rotary surgical assembly is a grater, such as an acetabular grater.

* * * * *